US012765112B2

(12) United States Patent
Lin

(10) Patent No.: US 12,765,112 B2
(45) Date of Patent: Oct. 13, 2026

(54) PHOTODIODE STRUCTURE AND MANUFACTURING METHOD THEREOF

(71) Applicant: Taiwan-Asia Semiconductor Corporation, Hsinchu City (TW)

(72) Inventor: Chun-Chieh Lin, Hsinchu City (TW)

(73) Assignee: Taiwan-Asia Semiconductor Corporation, Hsinchu City (TW)

( * ) Notice: Subject to any disclaimer, the term of this patent is extended or adjusted under 35 U.S.C. 154(b) by 425 days.

(21) Appl. No.: 18/495,100

(22) Filed: Oct. 26, 2023

(65) Prior Publication Data

US 2024/0145605 A1 May 2, 2024

(30) Foreign Application Priority Data

Nov. 2, 2022 (TW) ................................ 111141908

(51) Int. Cl.

| | |
|---|---|
| ***H01L 31/0216*** | (2014.01) |
| ***H10F 71/00*** | (2025.01) |
| ***H10F 77/30*** | (2025.01) |
| *A61B 5/1455* | (2006.01) |

(52) U.S. Cl.

CPC ........... *H10F 77/306* (2025.01); *H10F 71/00* (2025.01); *A61B 5/14551* (2013.01)

(58) Field of Classification Search

CPC .... H10F 77/306; H10F 71/121; H10F 30/221; H10F 71/00-1395; A61B 5/14551; A61B 5/14552; A61B 2562/0233; A61B 2562/12

See application file for complete search history.

(56) References Cited

U.S. PATENT DOCUMENTS 12,015,099 B2 * 6/2024 Liao ...................... H10F 39/811
2003/0139013 A1 7/2003 Kang et al.

FOREIGN PATENT DOCUMENTS

KR 10-2021-0070016 A 6/2021
TW I742841 B 10/2021

OTHER PUBLICATIONS

Office Action (with Search Report) issued in corresponding TW application No. 111141908 dated Apr. 7, 2023 (5 pages).

* cited by examiner

*Primary Examiner* — Cuong B Nguyen

(74) *Attorney, Agent, or Firm* — MUNCY, GEISSLER, OLDS & LOWE, P.C.

(57) ABSTRACT

A manufacturing method of a photodiode structure includes the following steps: providing a substrate; performing an epitaxial process to form a first semiconductor layer on the substrate; performing an active area patterning and etching process to form a recessed portion on the first semiconductor layer; performing a first coating process to form a first anti-reflection layer on the first semiconductor layer; and performing an ion implantation process to pass through the first anti-reflection layer and form a second semiconductor layer in the recessed portion.

11 Claims, 4 Drawing Sheets

PHOTODIODE STRUCTURE AND MANUFACTURING METHOD THEREOF

CROSS-REFERENCES TO RELATED APPLICATIONS

This application claims priority to Taiwan Patent Application No. 111141908 filed on Nov. 2, 2022, which is hereby incorporated by reference in its entirety.

BACKGROUND OF THE INVENTION

Field of the Invention

The present invention relates to a manufacturing method of a photodiode structure, especially a manufacturing method of a photodiode structure that is capable of maintaining high linearity.

Descriptions of the Related Art

Photodiodes are used to receive external light and output corresponding analog electrical signals or perform switching of different states in the circuit. Currently, photodiodes are widely used in products that require optical measurement. For example, many smart wearable devices use photodiodes to perform corresponding functions such as pulse and/or blood oxygen measurement.

In the process of conventional photodiodes, required N-type and P-type semiconductor layers are formed first, and then an anti-reflection layer is coated on the surface of these semiconductor layers. Since the materials and thicknesses used for each anti-reflection layer are different, the process of some anti-reflection layers may need to be carried out in a high temperature environment to facilitate the formation of the corresponding anti-reflection layer. However, these semiconductor layers may be affected by the high temperature of the process, which may cause material changes to easily have problems such as degradation of linearity, thus affecting the sensing performance of the photodiode.

Therefore, it is worthwhile to study how to design the manufacturing method of the photodiode structure that can resolve the aforementioned problems.

SUMMARY OF THE INVENTION

The objective of the present invention is to provide a manufacturing method of a photodiode structure that is capable of maintaining high linearity.

To achieve the above objective, the manufacturing method of the photodiode structure of the present invention includes the following steps: providing a substrate; performing an epitaxial process to form a first semiconductor layer on the substrate; performing an active area patterning and etching process to form a recessed portion on the first semiconductor layer; performing a first coating process to form a first anti-reflection layer on the first semiconductor layer; and performing an ion implantation process to pass through the first anti-reflection layer and form a second semiconductor layer in the recessed portion.

In an embodiment of the present invention, the first coating process is a high temperature LPCVD process.

In an embodiment of the present invention, a process temperature of the first coating process is not lower than 800° C.

In an embodiment of the present invention, the first anti-reflection layer has a thickness ranging between 20 and 30 nm.

In an embodiment of the present invention, the first anti-reflection layer is formed by a LPCVD process.

In an embodiment of the present invention, the manufacturing method further includes the following steps: performing a second coating process to form a second anti-reflection layer on the first anti-reflection layer; performing a first metallization process to form a first electrode electrically connected to the substrate; and performing a second metallization process to form a second electrode electrically connected to the second semiconductor layer.

In an embodiment of the present invention, the second coating process is a PVD process, and a process temperature of the second coating process is lower than the process temperature of the first coating process.

In an embodiment of the present invention, the process temperature of the second coating process is not higher than 200° C.

In an embodiment of the present invention, the second anti-reflection layer has a thickness ranging between 100 and 150 nm.

In an embodiment of the present invention, the first semiconductor layer is an N-type semiconductor layer, the second semiconductor layer is a P-type semiconductor layer, the first electrode is a negative electrode, and the second electrode is a positive electrode.

The present invention also includes a photodiode structure manufactured by the aforementioned manufacturing method.

Accordingly, by performing the high temperature coating process for forming the first anti-reflection layer before forming the second semiconductor layer, it can prevent the high temperature of the process from affecting the already-formed second semiconductor layer, and reduce the possibility of degradation of the linearity of the second semiconductor layer, thereby maintaining the original sensing performance of the photodiode structure of the present invention.

DETAILED DESCRIPTION OF THE PREFERRED EMBODIMENT

Since the various aspects and embodiments are merely illustrative and not restrictive, after reading this specification, there may also be other aspects and embodiments without departing from the scope of the present invention to a person having ordinary skill in the art. The features and advantages of these embodiments and the scope of the patent application will be better appreciated from the following detailed description.

Herein, “a” or “an” is used to describe one or more elements and components described herein. Such a descriptive term is merely for the convenience of illustration and to provide a general sense of the scope of the present invention. Therefore, unless expressly stated otherwise, the term “a” or “an” is to be understood to include one or at least one, and the singular form also includes the plural form.

Herein, the terms “first” or “second” and similar ordinal numbers are mainly used to distinguish or refer to the same or similar elements or structures, and do not necessarily imply the spatial or temporal order of such elements or structures. It should be understood that in certain situations or configurations, ordinal numbers may be used interchangeably without affecting the practice of the present invention.

As used herein, the term “comprise” “include,” “have” or any other similar term is not intended to exclude additional, unrecited elements. For example, a device or structure comprising/including/having a plurality of elements is not limited to the elements listed herein but may comprise/include/have other elements not explicitly listed but generally inherent to the element or structure.

The photodiode structure of the present invention can be applied to smart wearable devices. Smart wearable devices use photodiodes as optical sensors to measure body parameters such as pulse rate and/or blood oxygen saturation level. In order to maintain the stability of signal sensing and the accuracy of subsequent calculation and processing, it is necessary to maintain the high linearity of photodiodes. It should be explained here first that the aforementioned linearity refers to the ratio of the intensity of the received light source to the photocurrent generated by the photodiode itself, in which the smaller the ratio, the higher the linearity.

Figure 1:
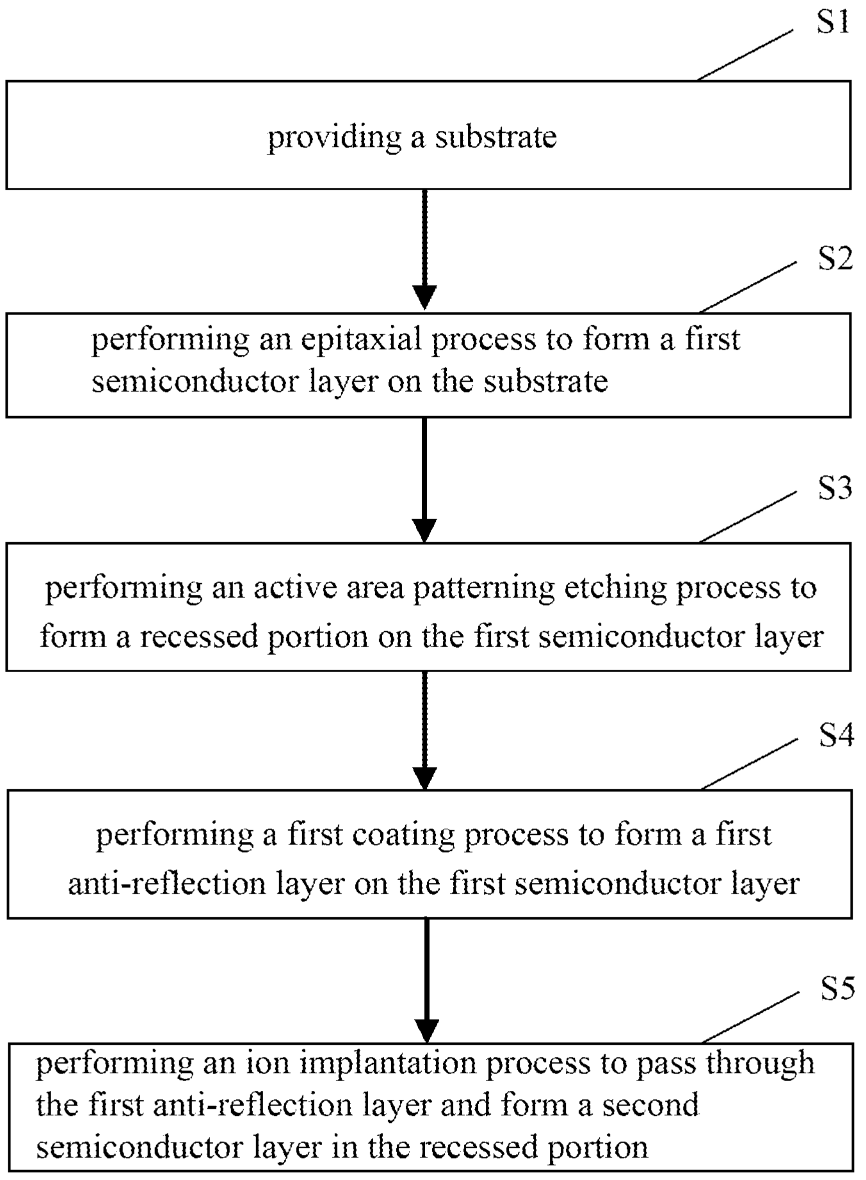
FIG. 1 is a flowchart of the manufacturing method of the photodiode structure of the present invention.
Figure 2A:
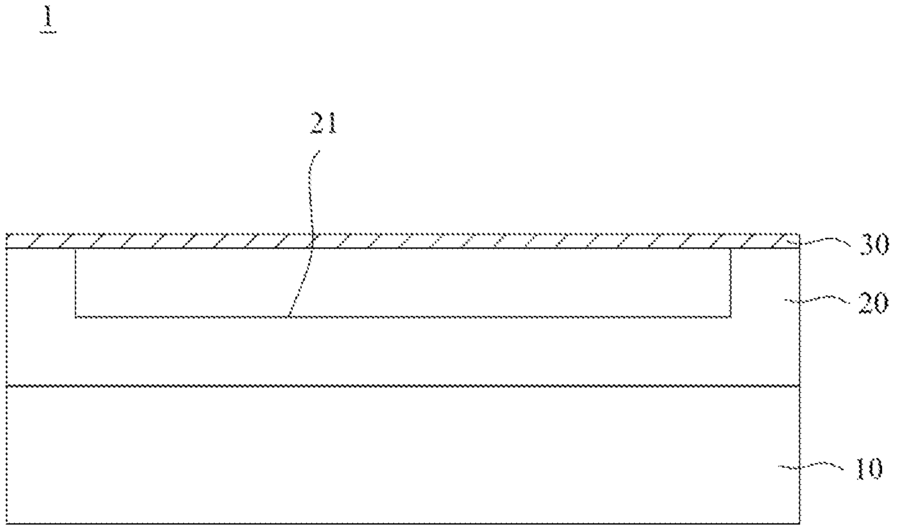
FIG. 2A is a schematic structural view of the photodiode structure of the present invention before forming the second semiconductor layer.
Figure 2B:
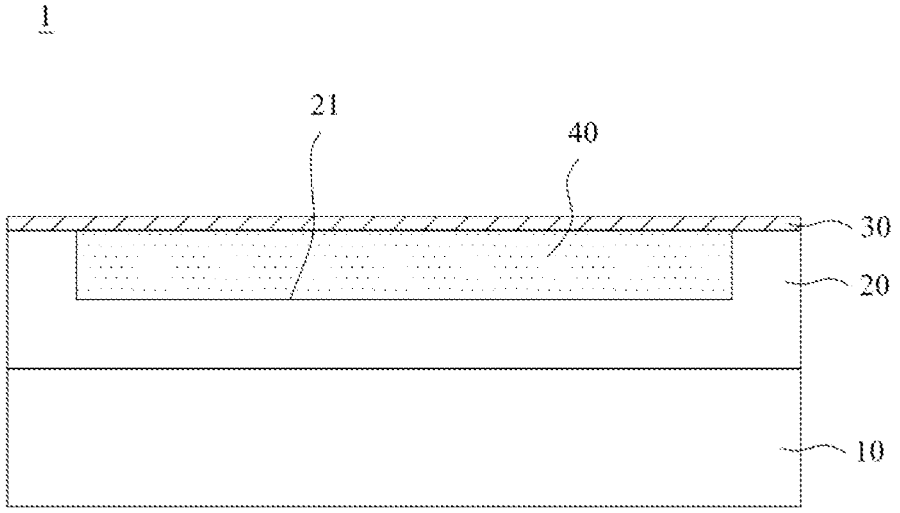
FIG. 2B is a schematic structural view of the photodiode structure of the present invention after forming the second semiconductor layer.

Please refer to FIG. 1 to FIG. 2B together for the following descriptions. FIG. 1 is a flowchart of the manufacturing method of the photodiode structure of the present invention. FIG. 2A is a schematic structural view of the photodiode structure of the present invention before forming the second semiconductor layer. FIG. 2B is a schematic structural view of the photodiode structure of the present invention after forming the second semiconductor layer. As shown in FIG. 1 to FIG. 2B, the manufacturing method of the photodiode structure of the present invention includes the following steps:

Step S1: providing a substrate.

Firstly, the present invention provides the substrate 10 as the basic structural member of the photodiode structure 1 of the present invention. The substrate 10 can be provided by using a semiconductor material process, such as a highly doped N-type semiconductor (i.e., an N+ semiconductor), but the selection of the aforementioned semiconductor material will vary according to different design requirements.

Step S2: performing an epitaxial process to form a first semiconductor layer on the substrate.

After the substrate 10 is provided in the above step S1, the present invention can then perform an epitaxial (EPI) process on one side of the substrate 10 to form the first semiconductor layer 20 on the substrate 10. The first semiconductor layer 20 can be formed by using a low-doped N-type semiconductor (i.e., an N-semiconductor) process, but the selection of the aforementioned semiconductor material will vary according to different design requirements.

Generally speaking, after the first semiconductor layer 20 is formed, an initial oxidation process will be performed on the surface of the exposed side of the first semiconductor layer 20 to form an oxide layer on the surface as an insulating layer. In the manufacturing method of the photodiode structure of the present invention, the same process can also be performed after the first semiconductor layer 20 is formed, but the present invention is not limited thereto.

Step S3: performing an active area patterning etching process to form a recessed portion on the first semiconductor layer.

After the first semiconductor layer 20 is formed in the above step S2, the present invention may then perform the active area patterning etching process on the surface of the exposed side of the first semiconductor layer 20, e.g., using the photolithography process on the first semiconductor layer 20 to form the necessary geometric structure of the active area. In the present invention, the first semiconductor layer 20 may at least form a recessed portion 21 after performing the active area patterning etching process for arranging the second semiconductor layer 40 described later (please refer to FIG. 2B).

Step S4: performing a first coating process to form a first anti-reflection layer on the first semiconductor layer.

After the above step S3, the present invention can then perform the first coating process on the surface of the exposed side of the first semiconductor layer 20 to form the first anti-reflection layer 30 on the first semiconductor layer 20. The first anti-reflection layer 30 can completely cover the recessed portion 21 of the first semiconductor layer 20. In the present invention, the first coating process adopts a low-pressure chemical vapor deposition (LPCVD) process, and the aforementioned LPCVD process is performed in a high temperature environment. The process temperature of the first coating process is not lower than 800° C. For example, in an embodiment of the present invention, the process temperature of the first coating process is about 800° C., but the present invention is not limited thereto. In addition, in an embodiment of the present invention, the first anti-reflection layer is mainly formed by the silicon nitride process that needs to be formed at high temperature, and the thickness of the first anti-reflection layer 30 formed by the first coating process ranges between 20 and 30 nm. For example, in an embodiment of the present invention, the thickness of the first anti-reflection layer 30 is about 25 nm, but the thickness of the first anti-reflection layer 30 can be changed with different materials or different design requirements.

Step S5: performing an ion implantation process to pass through the first anti-reflection layer and form a second semiconductor layer in the recessed portion.

After the first anti-reflection layer 30 is formed in the above step S4, the present invention can perform the ion implantation process at the position of the recessed portion 21 of the first semiconductor layer 20 to form the second semiconductor layer 40 in the recessed portion 21. With the aid of the high power of the ion implantation process, it allows the material for forming the second semiconductor layer 40 to pass through the first anti-reflection layer 30 to reach the recessed portion 21, thereby forming the second semiconductor layer 40 in the recessed portion 21.

It can be seen that, because the second semiconductor layer 40 is formed after forming the first anti-reflection layer 30 which needs to be treated at high temperature, the second semiconductor layer 40 will not be affected by the high temperature of the first coating process, so as to ensure that the material properties of the second semiconductor layer 40. As a result, the high linearity provided by the photodiode structure of the present invention is maintained.

Figure 3:
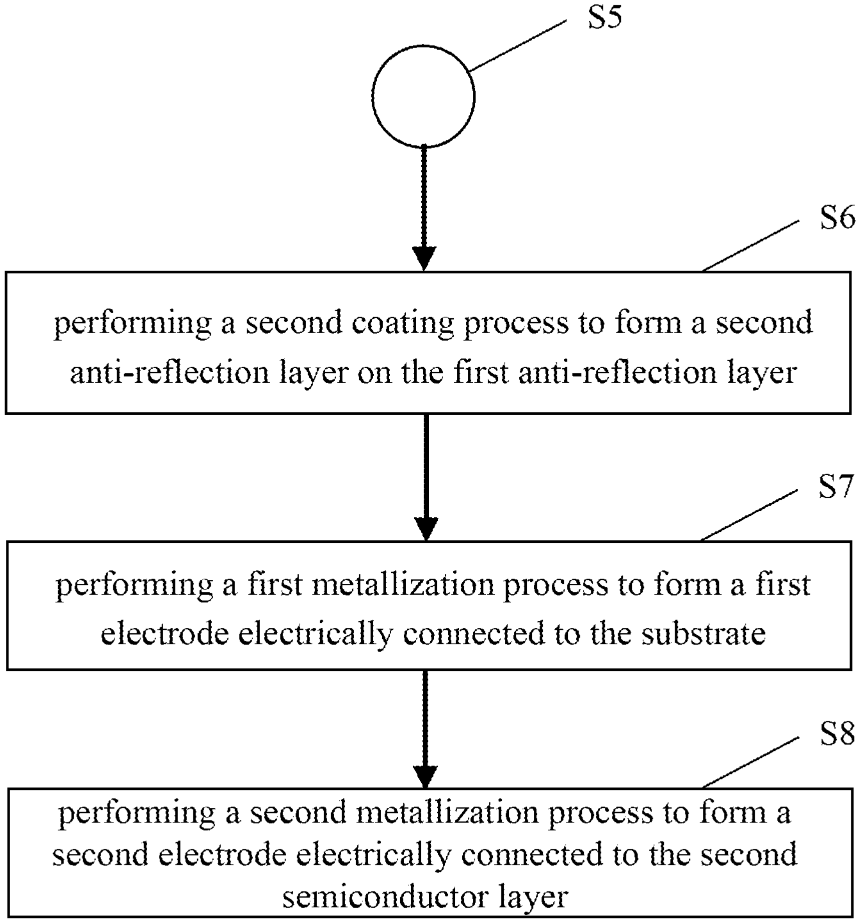
FIG. 3 is another flowchart of the manufacturing method of the photodiode structure of the present invention.
Figure 4:
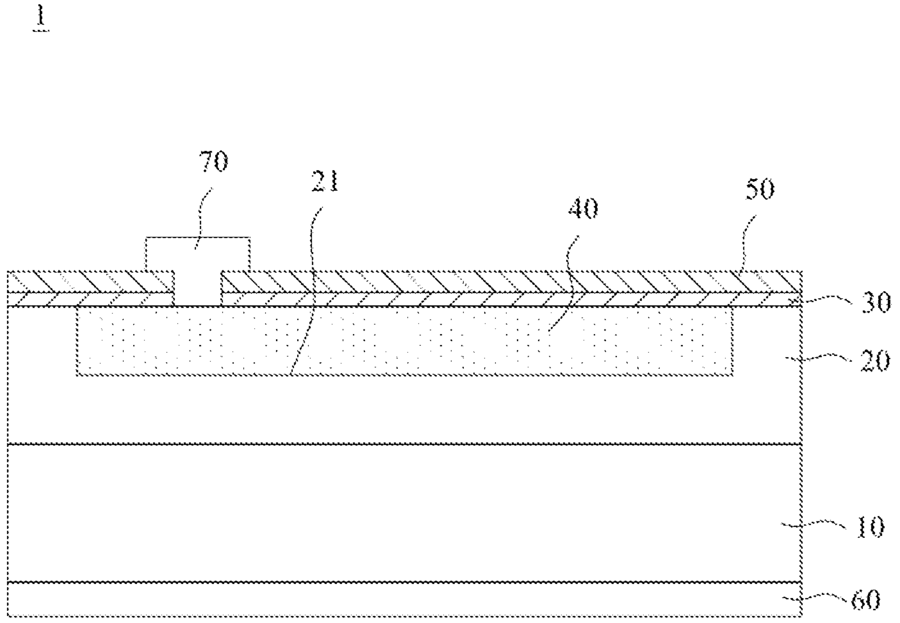
FIG. 4 is an overall schematic view of the photodiode structure of the present invention.

Please refer to FIG. 3 and FIG. 4 together for the following descriptions. FIG. 3 is another flowchart of the manufacturing method of the photodiode structure of the present invention, and FIG. 4 is an overall schematic view of the photodiode structure of the present invention. As shown in FIG. 3 and FIG. 4, the manufacturing method of the photodiode structure of the present invention also includes the following steps:

Step S6: performing a second coating process to form a second anti-reflection layer on the first anti-reflection layer.

After the second semiconductor layer 40 is formed in the above step S5, the present invention can then perform the second coating process on the surface of the exposed side of the first anti-reflection layer 30 to form the second anti-reflection layer 50 on the first anti-reflection layer 30. In the present invention, the second coating process adopts a physical vapor deposition (PVD) process, and the process temperature of the aforementioned PVD process is lower than the process temperature of the first coating process, wherein the process temperature of the second coating process does not affect the material properties of the second semiconductor layer 40 itself. The process temperature of the second coating process is not higher than 200° C. For example, in an embodiment of the present invention, the process temperature of the second coating process is about 200° C., but the present invention is not limited thereto. In addition, in an embodiment of the present invention, the second anti-reflection layer 50 is mainly formed by the PVD process. Accordingly, even if the second coating process is performed after the second semiconductor layer 40 is formed, the material properties of the second semiconductor layer 40 will not be affected by the process temperature of the second coating process.

Generally speaking, after the second anti-reflection layer 50 is formed, other single or multiple coating processes may be selectively performed depending on design requirements to further form more anti-reflection layers on the surface of the exposed side of the second anti-reflection layer 50, and the materials and processes used for these anti-reflection layers are also different from the aforementioned first coating process and second coating process. However, the process temperatures of these anti-reflection layers also belong to the temperatures which will not affect the material properties of the second semiconductor layer 40 itself.

Step S7: performing a first metallization process to form a first electrode electrically connected to the substrate.

After forming the second anti-reflection layer 50 in the above step S6, the present invention may then perform the first metallization process on the surface of the other exposed side of the substrate 10 to form the first electrode 60 on the other side of the substrate 10. That is to say, in structure, the first electrode 60 is formed below the substrate 10. In the present invention, the first electrode 60 is a negative electrode, but the present invention is not limited thereto.

Step S8: performing a second metallization process to form a second electrode electrically connected to the second semiconductor layer.

After forming the second semiconductor layer 40 in the above step S7, the present invention may perform the second metallization process on the surface of the exposed side of the second anti-reflection layer 50 to form the second electrode 70 on the second anti-reflection layer 50. In the practical manufacture of the structure, after being formed, the first anti-reflection layer 30 and the second anti-reflection layer 50 will have vias formed therein at the appropriate position above the second semiconductor layer 40 first, and then the second electrode 70 is formed by performing the second metallization process so that the second electrode 70 is electrically connected to the second semiconductor layer 40 through the vias. In the present invention, the first electrode 60 is a positive electrode, but the present invention is not limited thereto.

The present invention also includes a photodiode structure 1 manufactured by using the aforementioned manufacturing method. The structural features of the photodiode structure 1 of the present invention are shown in FIG. 2 or FIG. 4, and the forming methods of each detailed structure have been disclosed in the foregoing descriptions, and will not be repeated here.

The foregoing detailed description is illustrative in nature only and is not intended to limit the embodiments of the claimed subject matters or the applications or uses of such embodiments. Furthermore, while at least one exemplary embodiment has been presented in the foregoing detailed description, it should be appreciated that a wide variety of modifications to the present invention are possible. It should also be appreciated that the embodiments described herein are not intended to limit the scope, use, or configuration of the claimed subject matters in any way. Instead, the foregoing detailed description is intended to provide a person having ordinary skill in the art with a convenient guide for implementing one or more of the described embodiments. Moreover, various modifications may be made in the function and arrangement of the elements without departing from the scope defined by the claims, including known equivalents and any equivalents that may be anticipated at the time of filing this patent application.

What is claimed is:

1. A manufacturing method of a photodiode structure, comprising:
- providing a substrate;
- performing an epitaxial process to form a first semiconductor layer on the substrate;
- performing an active area patterning etching process to form a recessed portion on the first semiconductor layer;
- performing a first coating process to form a first anti-reflection layer on the first semiconductor layer;
- performing an ion implantation process to pass through the first anti-reflection layer and form a second semiconductor layer in the recessed portion;
- performing a second coating process to form a second anti-reflection layer on the first anti-reflection layer;
- performing a first metallization process to form a first electrode electrically connected to the substrate; and
- performing a second metallization process to form a second electrode electrically connected to the second semiconductor layer.

2. The manufacturing method of claim 1, wherein the first coating process is a high temperature low-pressure chemical vapor deposition process.

3. The manufacturing method of claim 2, wherein a process temperature of the first coating process is not lower than 800° C.

4. The manufacturing method of claim 1, wherein the first anti-reflection layer has a thickness ranging between 20 nm and 30 nm.

5. The manufacturing method of claim 1, wherein the first anti-reflection layer is formed by a low-pressure chemical vapor deposition process.

6. The manufacturing method of claim 1, wherein the second coating process is a physical vapor deposition process, and a process temperature of the second coating process is lower than a process temperature of the first coating process.

7. The manufacturing method of claim 6, wherein the process temperature of the second coating process is not higher than 200° C.

8. The manufacturing method of claim 1, wherein the second anti-reflection layer has a thickness ranging between 100 nm and 150 nm.

9. The manufacturing method of claim 1, wherein the second anti-reflection layer is formed by a physical vapor deposition process.

10. The manufacturing method of claim 1, wherein the first semiconductor layer is an N-type semiconductor layer, the second semiconductor layer is a P-type semiconductor layer, the first electrode is a negative electrode, and the second electrode is a positive electrode.

11. A photodiode structure manufactured by using the manufacturing method of claim 1.

* * * * *